United States Patent
Paul et al.

(10) Patent No.: US 11,071,502 B2
(45) Date of Patent: Jul. 27, 2021

(54) METHOD AND APPARATUS FOR CHARACTERIZING AN OBSTACLE WITHIN AN EXAMINATION OBJECT USING A MEDICAL IMAGE DATA SET

(71) Applicant: Siemens Healthcare GmbH, Erlangen (DE)

(72) Inventors: Dominik Paul, Bubenreuth (DE); Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 283 days.

(21) Appl. No.: 16/207,355

(22) Filed: Dec. 3, 2018

(65) Prior Publication Data
US 2019/0167203 A1    Jun. 6, 2019

(30) Foreign Application Priority Data
Dec. 4, 2017    (DE) .......................... 102017221830.4

(51) Int. Cl.
| | | |
|---|---|---|
| *G06K 9/00* | (2006.01) | |
| *A61B 5/00* | (2006.01) | |
| *A61B 5/055* | (2006.01) | |
| *G01R 33/54* | (2006.01) | |
| *G01R 33/56* | (2006.01) | |

(52) U.S. Cl.
CPC ............ *A61B 5/7267* (2013.01); *A61B 5/055* (2013.01); *G01R 33/543* (2013.01); *G01R 33/5608* (2013.01)

(58) Field of Classification Search
CPC ..................................................... G16H 50/70
See application file for complete search history.

(56) References Cited

U.S. PATENT DOCUMENTS

| | | | |
|---|---|---|---|
| 8,884,618 B2 * | 11/2014 | Mahfouz | A61F 2/3601 |
| | | | 324/309 |
| 10,825,168 B2 * | 11/2020 | Tegzes | G06T 7/11 |
| 2013/0177230 A1 * | 7/2013 | Feng | G06T 7/0012 |
| | | | 382/132 |
| 2015/0362578 A1 | 12/2015 | Biber et al. | |
| 2017/0150937 A1 | 6/2017 | Stille et al. | |
| 2018/0256611 A1 * | 9/2018 | Tabuteau | A61K 31/675 |
| 2018/0374245 A1 * | 12/2018 | Xu | A61B 6/5282 |
| 2019/0164288 A1 * | 5/2019 | Wang | G06T 5/002 |

FOREIGN PATENT DOCUMENTS

| | | |
|---|---|---|
| DE | 102008036814 A1 | 2/2010 |
| DE | 102012214593 A1 | 8/2013 |

* cited by examiner

*Primary Examiner* — Oneal R Mistry
(74) *Attorney, Agent, or Firm* — Schiff Hardin LLP

(57) ABSTRACT

In a method and apparatus for characterizing an obstacle within an examination object using a medical image data set by the use of a database containing at least one data class, a trained artificial neural network defines and develops relationships between different obstacles, features and medical imaging data sets. A data entry of a data class is assigned by the neural network to the obstacle within the examination object and the obstacle within the examination object is characterized in an electronic output by this data entry.

19 Claims, 2 Drawing Sheets

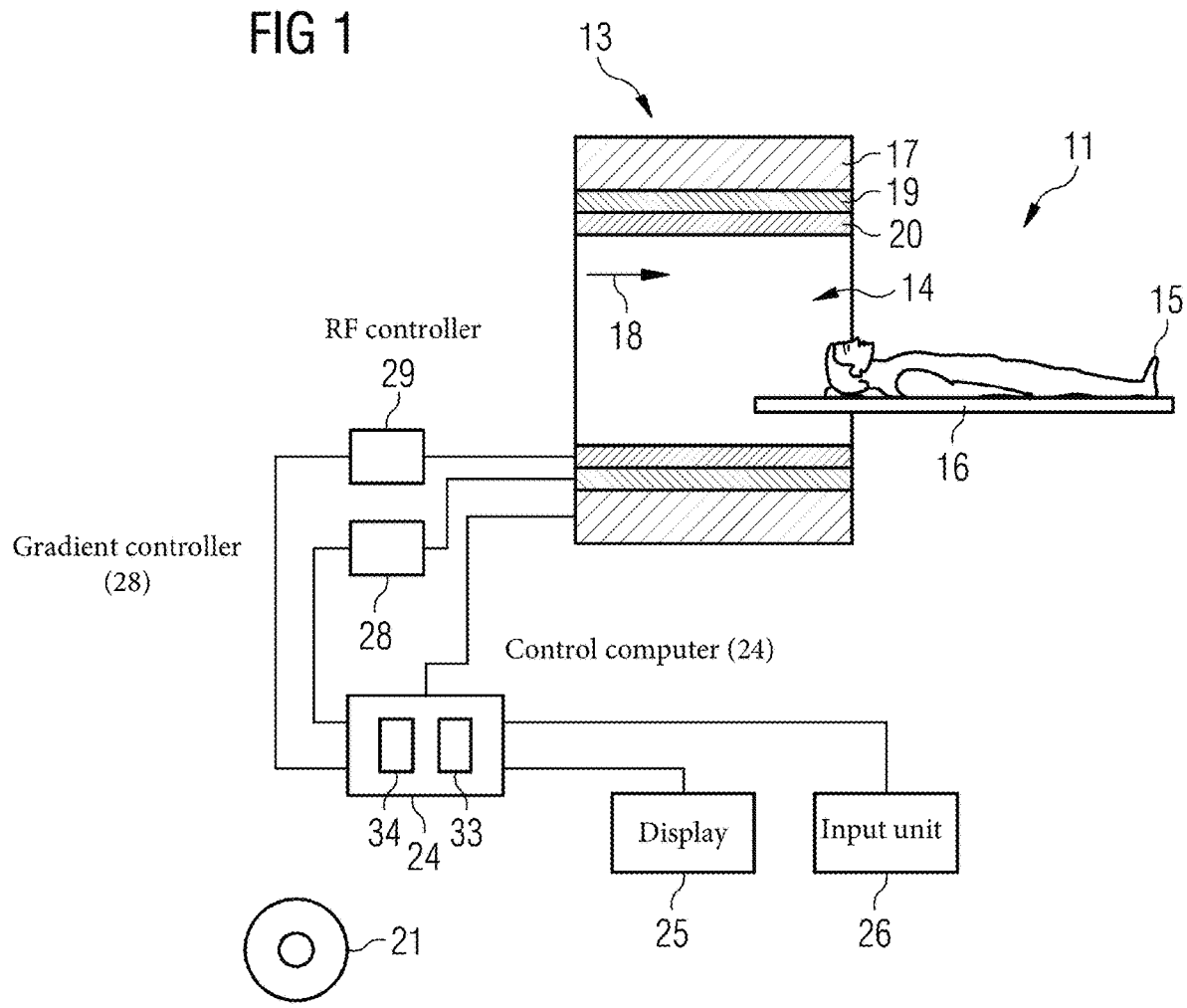

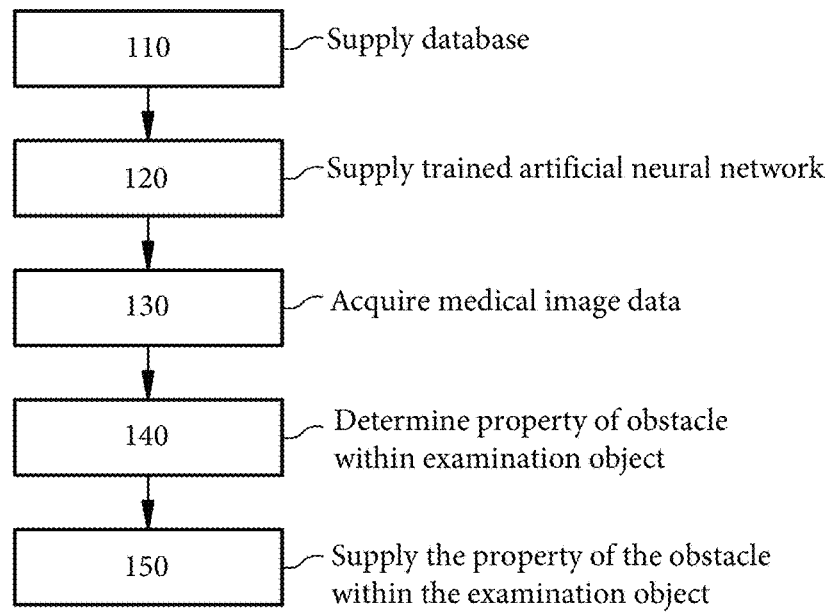
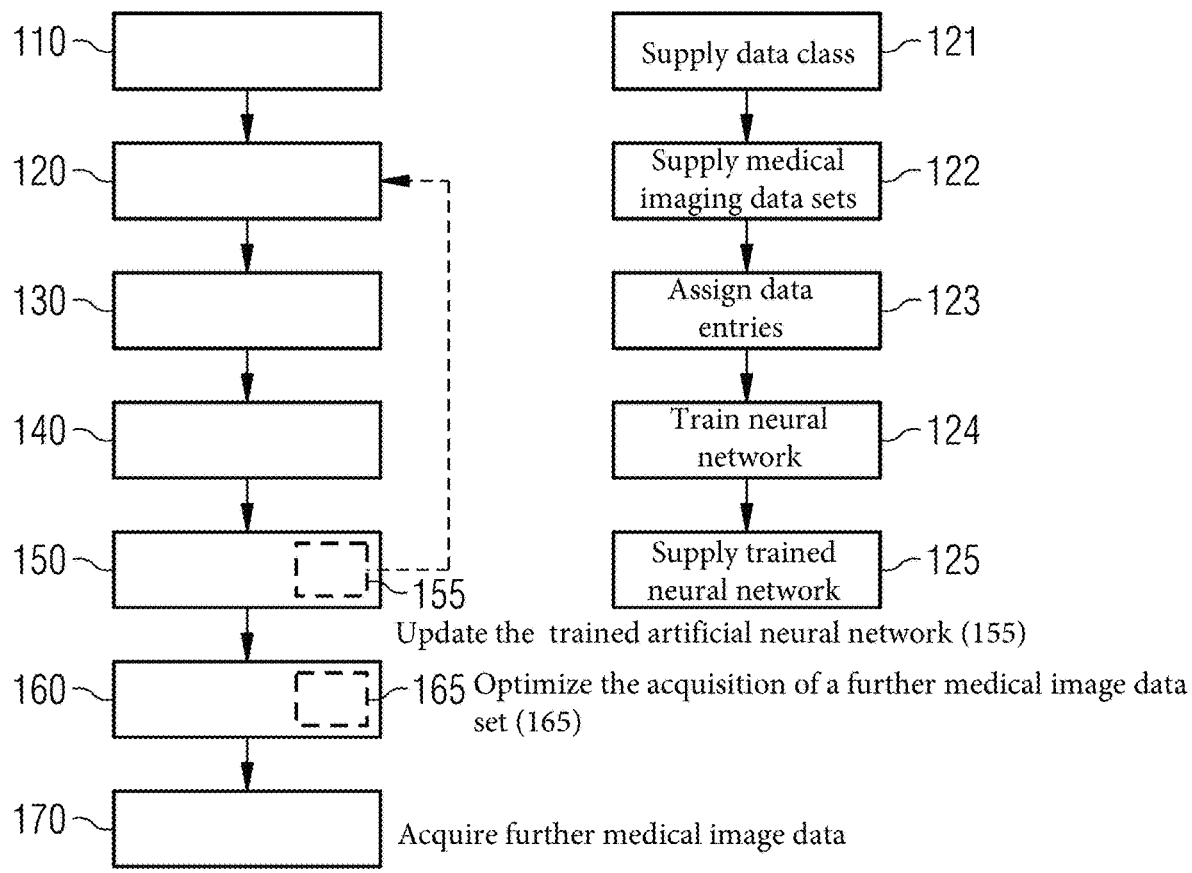

METHOD AND APPARATUS FOR CHARACTERIZING AN OBSTACLE WITHIN AN EXAMINATION OBJECT USING A MEDICAL IMAGE DATA SET

BACKGROUND OF THE INVENTION

Field of the Invention

The invention concerns a method, a medical imaging apparatus, a computer, and a non-transitory, electronically readable data carrier, for characterizing an obstacle within an examination object.

Description of the Prior Art

Medical imaging apparatuses, for example a magnetic resonance apparatus, a Single Photon Emission Computed Tomography (SPECT) apparatus, a Positron Emission Tomography (PET) apparatus, a computed tomography (CT) apparatus, an ultrasound device, an X-ray apparatus, a C-arm device, or a combined medical imaging apparatus, formed by any combination of such apparatus are suitable for generating a medical image data set.

In a magnetic resonance apparatus, the body of an examination object to be examined, such as a patient, is conventionally exposed to a strong basic magnetic field, for example of 1.5 or 3 or 7 tesla, produced by a basic field magnet. In addition, gradient pulses are activated by a gradient coil arrangement. Radio-frequency (RF) pulses, for example excitation pulses, are then emitted by a radio-frequency antenna by suitable coils, which leads to nuclear spins of particular atoms, which are resonantly excited by these radio-frequency pulses, being tilted by a defined flip angle with respect to the magnetic field lines of the basic magnetic field. With relaxation of the nuclear spins, radio-frequency signals, known as magnetic resonance signals, are emitted and are received by a suitable radio-frequency antenna, and then processed further. The desired image data can be reconstructed from the raw data acquired in this way.

For a particular scan, a specific magnetic resonance control sequence (MR control sequence), also called a pulse sequence, should therefore be emitted, which includes a sequence of radio-frequency pulses, for example excitation pulses and refocusing pulses, as well as gradient pulses that are to be emitted appropriately coordinated therewith in different gradient axes along different spatial directions. Appropriately timed readout windows are set which specify the periods in which the induced magnetic resonance signals are acquired.

An examination object is typically a patient. The method disclosed herein concerns an examination object that has an obstacle therein. Obstacles can be, for example, implants in the human body. Obstacles typically have at least one material that is not tissue, is not a material naturally occurring in the human and/or animal body and/or examination object. Typical obstacles are implants made from metal and/or ceramic and/or silicone. Frequently used implants, in other words obstacles, are, for example, artificial knee joints, hip joints, breast implants, screws.

Obstacles of this kind typically influence medical imaging and can generate artifacts in the corresponding image data. Influences or artifacts of this kind is/are dependent on the medical imaging apparatus, typically also on the recording technique and the obstacle itself. In image data generated with a magnetic resonance apparatus, metal implants, such as artificial hip joints, cause a volume-like signal cancellation, whereas a strip-like signal cancellation is caused in image data generated with a computed tomography. Recording techniques are known in order to reduce such artifacts, depending on the modality of the medical imaging apparatus. In the case of computed tomography systems having an elevated radiation dose, and in the case of magnetic resonance apparatuses these techniques typically result in a prolonged length of the examination for the examination object, and/or blurring of the image data.

In magnetic resonance imaging in particular, specific recording techniques (MR control sequences) have been developed in order to reduce such artifacts. Examples of this are "Multi Acquisition Variable Resonance Image Combination" (MAVRIC), "Slice Encoding Metal Artifact Correction" (SEMAC), "View Angle Tilting" (VAT). Another approach is to use MR control sequences of a type that are not seriously affected by the presence of obstacles, such as "Turbo Spin Echo" (TSE). Preferably "Short T1 Inversion Recovery" (STIR) or "Spectral Attenuated Inversion Recovery" (SPAIR) is used for fat saturation.

As noted, recording techniques for reducing the artifacts are associated with various drawbacks. Furthermore, the effectiveness of such recording techniques for reducing the artifacts is dependent on the obstacle. Different obstacles cause artifacts of different severity. It is therefore advantageous to acquire knowledge about an obstacle in the examination object, in particular in the examination region, before beginning recording of diagnostic image data. Based on this knowledge, a suitable recording technique can be selected for acquisition of the diagnostic image data. Diagnostic image data typically represent a section of the examination object, with particular an examination region, with a contrast and/or with a spatial resolution such that an expert, for example a doctor, can make a diagnosis based on the diagnostic image data.

Methods for characterizing obstacles are known for magnetic resonance imaging. Examples are disclosed in US20150177354A1 and DE102013205930B4.

SUMMARY OF THE INVENTION

An object of the invention is to provide a particularly efficient method for characterizing an obstacle within an examination object.

The inventive method for characterizing an obstacle within an examination object using a medical image data set has the following steps.

A database is generated so as to have at least one data class for a feature that characterizes different obstacles. The data class has at least one data entry for each of the different obstacles.

A trained artificial neural network is provided that is trained for relationships between the different obstacles, the feature, and a medical image data set.

A medical image data set is acquired from an examination object that has an obstacle therein.

A property of the obstacle within the examination object is determined by applying the trained artificial neural network to the medical image data set, with a data entry of the data class thereby being assigned to the obstacle within the examination object, and the obstacle within the examination object is characterized by this data entry.

An electronic output of the property of the obstacle within the examination object.

The examination object is typically a patient. Image data are typically generated from the examination object in the course of an examination with a medical imaging device.

The image data are typically generated from a detail of the examination object, an examination region. The acquired medical image data preferably represent an examination region of the examination object. The examination region of the examination object includes the obstacle.

The medical image data set contains image data that represent the examination object, in particular the examination region and the obstacle. The medical image data set can be present before the beginning of the inventive method, in particular can have been generated in advance with a first medical imaging device and/or be supplied to a computer that performs the inventive method, in the form of a data file. Acquisition of the medical image data set can also be implemented as part of the method. The medical image data set can contain multiple subsets of medical image data respectively acquired by different medical imaging devices.

The medical image data set can be image data acquired in of an overview scan. Overview scans are typically characterized by being acquired more quickly and/or with lower resolution than diagnostic image data. The medical image data set can be diagnostic image data acquired from the examination object at an earlier time, for example in the course of a preceding examination.

An obstacle is typically characterized by a number of features. Each of these features is preferably stored as a data entry in the database. The database preferably has data entries for a number of obstacles, with each data entry describing a feature of an obstacle. Data entries that describe an identical feature of different obstacles are incorporated by a data class. Therefore, a first data class can include, for example, the data entries that describe the materials of the multiple obstacles. A data entry of the first data class then describes the material of one of the multiple obstacles. The database is stored as a data file such that, when carrying out the inventive method, the database can be accessed and data entries can be read from the database.

Another feature for characterizing an obstacle indicates a physical property of the obstacle. A feature for characterizing an obstacle indicates a measure of an interaction of the obstacle with the environment of the obstacle within an examination object and/or quantifies an interaction of this kind.

The trained artificial neural network contains information with respect to relationships and/or interactions between the different obstacles, the feature, and the medical image data set. The trained artificial neural network contains information with respect to the data entries and/or features incorporated by the database. The trained artificial neural network is designed to extract information from the medical image data set when applied to the medical image data set. The trained artificial neural network preferably has a visual intelligence. The trained artificial neural network is preferably designed to analyze information of this kind in the course of determining a property of the obstacle within the examination object and of identifying at least one corresponding data entry in the database. The at least one corresponding data entry can indicate a feature of the obstacle and/or be capable of determining a property of the obstacle.

A property of the obstacle within the examination object determined in the course of the inventive method can be a feature that characterizes an obstacle according to a data entry and/or be a combination of a number of data entries of the data class corresponding to the feature. The determined property of the obstacle within the examination object can also be a number of features for characterizing an obstacle. A number of features of this kind are incorporated by data entries of different data classes. Preferably at least one feature of at least one data class is assigned as the property to the obstacle within the examination object.

Supplying the property of the obstacle within the examination object means storing the property in a memory or a data carrier. Similarly, supplying can be transmission to a control computer and/or acquisition unit.

According to the inventive method, artifacts can be analyzed for a medical image data set acquired in the course of an overview scan using the trained artificial neural network. The analysis can be, for example, identifying signal cancellations and/or an analysis of the shape and/or size of the identified signal cancellations. Therefore, a signal cancellation can be in the form of a dipole, for example in the case of image data recorded with a magnetic resonance scanner, having a metal hip implant. Using the trained artificial neural network, signal cancellations of this kind can be assigned to an obstacle incorporated by the database. Therefore, the obstacle in the examination object can be identified. The trained artificial neural network preferably contains relationships between obstacles and signal cancellations for this. The trained artificial neural network is preferably trained in advance using different obstacles.

An advantage of the inventive method is that an obstacle in the examination object can be detected and identified. A property of the obstacle can be determined and supplied. It can consequently be ensured that artifacts are reduced in the case of subsequent acquisitions of image data. The safety of the examination object can also be increased. If the acquired medical image data set has been acquired by computed tomography and a ferromagnetic implant was identified as the obstacle, then the examination object can be excluded from future examinations that will use a magnetic resonance scanner. Ferromagnetic implants are contraindicative for examinations by a magnetic resonance. The inventive method enables a particularly efficient method for characterizing an obstacle within an examination object.

In an embodiment of the method, a feature for characterizing different obstacles is selected from the following list:
- material of the obstacle
- shape of the obstacle
- size of the obstacle
- producer of the obstacle
- effect of the obstacle on a medical image data set as a function of a medical imaging device and/or recording technique used for generating the medical image data set,
- a typical position and/or orientation and/or environment of the obstacle within the examination object.

A recording technique involves the acquisition of an image data set. Image data sets can be acquired by operation of a medical imaging apparatus (typically the scanner thereof) using different recording techniques. A magnetic resonance apparatus, for example, can be controlled using different MR control sequences. The parameterization of an MR control sequence of this kind can be decisive for the diagnosis. The features, cited in the list, that characterize different obstacles are preferably each compiled in a data class of the database and supplied to the inventive method. Preferably at least one feature of at least one data class is assigned as a property to the obstacle within the examination object. The obstacle within the examination object is preferably characterized by at least two features cited in the list, with each of the at least two features cited in the list being given by a physical variable and/or unique description. Therefore, for example using a signal evaluation it can be detected whether the obstacle is a knee or hip implant and as a function thereof, knowledge about the examination region can be obtained. Similarly, it can be detected whether the obstacle is a screw and/or a full implant, such as a hip joint. Titanium, stainless steel, and cobalt-chromium are frequently used as such material.

The trained artificial neural network is designed to identify the position and/or orientation of the obstacle within the examination object. Information with respect to the examination region is indirectly obtained thereby. A recording technique for acquisition of further image data can consequently be selected on the basis from recording techniques that are typical for this examination region. The obstacle can be characterized particularly accurately and extensively according to this embodiment of the method.

In an embodiment of the method, supplying the property of the obstacle includes updating the trained artificial neural network while considering the supplied property.

The supplied trained artificial neural network can be trained in the course of this embodiment of the method so that the information about the properties of the obstacle and the medical image data set, obtained when carrying out the method, is used for developing the trained artificial neural network. As a result, the trained artificial neural network is improved and has more information available for future executions of the inventive method. This enables improved characterizing of an obstacle within an examination object in future executions of the inventive method.

In another embodiment of the method, in a further method step, a method for acquisition of a further medical image data set is selected on the basis of the supplied property.

According to this embodiment, acquisition of a further medical image data set of the examination object containing the obstacle is planned on the basis of the characterized obstacle. Accordingly, a further medical image data set is acquired according to this embodiment in addition to characterizing of the obstacle. The further medical image data set preferably represents an examination region of the examination object comprising the obstacle with an image quality suitable for making a methodical diagnosis therefrom. The method for acquisition of the further medical image data set is preferably chosen such that artifacts in the further medical image data set are as few as possible. Selection of a method for acquisition of a further medical image data set can be selection of a modality of a medical imaging device, a recording technique available on the selected medical imaging device, and/or a parameter of the recording technique.

The selection can be made by a medical expert, or selection can be made automatically. The selection can be made on the basis of specifications by a user, in particular a medical expert. A table of associations between methods for acquisition of a further medical image data set properties of obstacles can be considered during selection. A further trained artificial neural network can be used during this selection, which preferably uses relationships between a supplied property of the characterized obstacle and a number of methods for acquisition of a further medical image data set. The further trained artificial neural network can be incorporated in the originally-described trained artificial neural network.

The method for acquisition of the further medical image data set is preferably designed so that artifacts based on the obstacle are efficiently reduced. A method for acquisition of this kind may have certain drawbacks associated therewith. Such drawbacks can be considered during the selection. During selection of the methods for acquisition, preferably their efficiency with respect to the reduction of artifacts based on the obstacle and drawbacks associated with the method for acquisition are considered.

A user, such as a medical expert, can specify at least one criterion that is considered during selection. Typical criteria relate to the quality of the further image data set and/or the duration of acquisition and/or the medical imaging device to be used. Therefore, the user can indicate for example a maximum length of an examination and a desired maximum signal cancellation. The method for acquisition of the further medical image data set can be selected on the basis of this. Criteria specified by the user can be weighted differently in this case. The selection can also be made automatically. Similarly, the selection can rule out a medical imaging device for acquisition of the further medical image data set if it is dangerous for the examination object and/or impermissible.

Furthermore, information with respect to the examination region itself is preferably considered during selection. Knowledge about a typical parameterization for acquisition of such an examination region in the absence of an obstacle can be considered during selection, in particular during selection of suitable parameters for acquisition.

An advantage of this embodiment is that the properties supplied according to the inventive method can advantageously be used for a further acquisition. It can thereby be ensured that the examination object, in particular the examination region, comprising the obstacle can be displayed in an optimum quality and/or a quality desired by the user during acquisition of a further medical image data set. Repetition of acquisition of the further medical image data set can be avoided thereby. The overall length of examination of an examination object can be reduced and/or efficiently used thereby. This is convenient and/or cost-efficient.

In another embodiment of the method, the selection includes optimization of a method for acquisition of a further medical image data set.

In particular, a criterion specified by a user, optionally with a weighting, can be considered during this optimization. Therefore, according to this embodiment, advantages and drawbacks of a method for acquisition of a further medical image data set, for example in respect of artifacts, length of examination and image quality, can generally be weighted. The further medical image data set can thereby be acquired especially individually and/or so as to be matched to the wishes of a user. Optimization can in particular relate to specific parameters during acquisition relating to the image quality, such as the image contrast.

One embodiment of the method provides that a further medical image data set is acquired according to the selected method. An advantage of this embodiment is that the properties supplied according to the inventive method can advantageously be used for a further acquisition. It can thereby be ensured that the examination object, in particular the examination region, comprising the obstacle can be displayed in an optimum quality and/or a quality desired by the user during acquisition of a further medical image data set. Repetition of acquisition of the further medical image data set can be avoided thereby. The overall length of examination of an examination object can be reduced and/or efficiently used thereby. This is convenient and/or cost-efficient.

In another embodiment of the method, the medical image data set and the further medical image data set are acquired with an identical medical imaging apparatus (scanner). According to the inventive method, the original medical image data set can have been acquired before acquisition thereof with a first medical imaging device. According to this embodiment, this first medical imaging device is also used for acquisition of the further medical image data set. According to this embodiment, the medical image data set was acquired with the first medical imaging device preferably in the course of an overview scan. As noted, the further medical image data set preferably is diagnostic image data. This corresponds to the typical sequence in a conventional examination. Parameters and/or recording techniques for acquisition of the diagnostic image data, in other words for acquisition of the further medical image data set, are determined on the basis of image data of an overview scan. This embodiment enables a method for acquisition of the diagnostic image data that is individually matched to an existing obstacle, so the examination is particularly efficient. In addition, diagnostic image data acquired in this way can have an optimum quality with a given length of an examination.

In another embodiment of the method, the further medical image data set is acquired with a medical imaging apparatus that is a magnetic resonance apparatus and acquisition of the further medical image data set is carried out according to one of the following MR control sequences and/or recording techniques:

TSE
VAT
SEMAC
MAVRIC
STIR
SPAIR
DIXON
Saturation pulses with different resonance frequency.

Such MR control sequences and/or recording techniques can reduce artifacts caused by obstacle to differing extents. In the course of this embodiment of the method, at least one parameter of the MR control sequences and/or recording techniques can be determined that is relevant to at least one parameter during acquisition of the further medical image data set. The extent of the correction of artifacts is typically scaled with the duration of acquisition of the further medical image data set. If, for example, it was detected during characterizing of the obstacle that the obstacle is a screw made from titanium having a length of 5 cm, then VAT can be selected as the method for acquisition of the further medical image data set. If, for example, it was detected during characterizing of the obstacle that the obstacle is a hip implant made from cobalt-chromium, then SEMAC and/or MAVRIC can be selected as the method for acquisition of the further medical image data set. If, for example, it was detected during characterizing of the obstacle that the obstacle is a breast implant made from silicone, then TSE and/or SPAIR and/or DIXON and/or saturation pulses having different resonance frequency can be selected as the method for acquisition of the further medical image data set.

Due to the phenomenon known as chemical shift, silicone can influence an adjustment of the system frequency of the magnetic resonance scanner, so artifacts are generated when an incorrect system frequency is used. In addition, suppression of silicone in the image can be insufficient. Silicone is typically displayed in the medical image data set as a homogeneous, closed region, so silicone can be easily detected. Based on information about the presence of silicone, an appropriate MR control frequency and/or an appropriate parameterization of an MR control frequency and/or selection of an appropriate sequence module for suppressing silicone and/or fat can be suggested to a user, and/or be selected.

An advantage of this embodiment is that artifacts in the magnetic resonance image emanating from an individual obstacle can be reduced particularly efficiently by the selection of a suitable MR control frequency and/or recording technique. Selection of the suitable MR control frequency and/or recording technique is preferably governed by the signal cancellations to be expected owing to the material and/or size of the obstacle.

In another embodiment of the method, supplying the trained artificial neural network involves the following method steps.

A data class is provided to the processor that includes a data entry of each of a number of different obstacles, each data entry being for a feature that characterizes the respective different obstacle.

The processor is supplied with a number of medical training image data sets.

Respective data entries in the class are assigned to the medical training image data sets.

The artificial neural network is trained using the image content of the medical training image data sets and the data entries respectively assigned thereto, so that the trained artificial neural network then enables an assignment of a data entry to a respective future medical image data set.

The trained artificial neural network is used for characterizing an obstacle within the examination object.

Therefore, the image content of the multiple medical training image data sets, to which the associated data entries of the data class have been respectively assigned, are decisive for training the artificial neural network. The medical training image data sets can be formed by medical imaging data sets that have already been recorded by medical imaging devices, possibly from different manufacturers. The medical training image data sets are preferably image data sets of examination regions each comprising at least one obstacle. The data entries cam be assigned to the medical training image data sets manually or semi-automatically, preferably as described below. The data entries can be assigned to the medical training image data sets, for example by a manufacturer of the medical imaging device, or by using characterization software, or by staff in a hospital.

Following assignment of the data entries to the medical training image data sets, the medical training image data sets then are known as labeled medical training image data sets. "Labeled" means that the expected feature of the obstacle, in other words the data entry associated with the medical training image data set, is given to each medical training image data set as a label.

The artificial neural network is preferably trained by backpropagation. This means that the image content of the multiple medical training image data sets is fed as input data into the artificial neural network to be trained. During training, an output of the artificial neural network to be trained is compared with the data entries (the labels) assigned to the multiple medical imaging data sets. Training of the artificial neural network then involves a change in the network parameters of the artificial neural network being trained such that the output of the artificial neural network being trained is closer to the data entries assigned to the respective medical imaging data sets. In this way the artificial neural network is trained such that it assigns the appropriate labels to the image content of the multiple medical image data sets. While backpropagation is the most important training algorithm for training an artificial neural network, other algorithms are known to those skilled in the art, which can also be used. Examples of other possible algorithms are evolutionary algorithms, "simulated annealing", "Expectation Maximization" algorithms (EM algorithms), parameter-free algorithms (non-parametric methods), Particle Swarm Optimization (PSO), etc.

The artificial neural network can be trained completely by the producer of the medical imaging devices and/or the characterization software. Alternatively, pre-training can be applied by the producer of the medical imaging device and/or the characterization software, and a post-training is then applied once or several times in a hospital in order to make the appropriate characterizing of an obstacle even more robust, specifically for the requirements of the hospital. Similarly, an already trained artificial neural network cane be re-classified by bringing in new weighting matrices for a different characterizing task. It is also possible for the artificial neural network to be trained in a number of iterations. In this way the data entries can be alternately assigned to the medical training image data sets in a number of steps in order to train the artificial neural network. Accuracy in the characterizing of the medical image data set by the trained artificial neural network thus can be improved.

The artificial neural network trained in this way can then be used in an inventive method for characterizing an obstacle within an examination object, according to any of the preceding embodiments. In this way the described training of the artificial neural network subsequently enables particularly advantageous characterizing of obstacles for which the associated data entries are still not known in advance.

In another embodiment of the method for supplying a trained artificial neural network, training of the artificial neural network involves a change in network parameters of the artificial neural network such that, when the trained artificial neural network is applied to the image content of the multiple medical training image data sets, the artificial neural network allocates the data entries to the multiple medical training image data sets. The process of backpropagation described here provides a particularly advantageous possibility for training the artificial neural network. The artificial neural network can also be flexibly trained for different characterizing tasks as a function of the supplied medical training image data sets and the assigned data entries.

In another embodiment of the method for supplying a trained artificial neural network, before supplying the trained artificial neural network, the validity of the trained artificial neural network is checked. For checking the validity of the artificial neural network, data entries are determined for some of the medical training image data sets by the trained artificial neural network, and the data entries determined in this way are compared with the data entries assigned to some of the medical training image data sets. This check can ensure that the trained artificial neural network is capable of characterizing obstacles using a medical image data set in which the actual data entry is a priori unknown.

The inventive characterization computer for characterizing an obstacle within an examination object has a first supply processor or circuit, a second supply processor or circuit, a third supply processor or circuit, an acquisition processor or circuit, a determining processor or circuit, and a third supply processor or circuit, with the characterization computer being configured overall for executing the inventive method for characterizing an obstacle within an examination object.

The first supply processor is designed for supplying a database having at least one data class for a feature that characterizes different obstacles, the data class containing at least one data entry respectively for each obstacle. The second supply unit is designed to supply a trained artificial neural network for relationships between the different obstacles, the feature and the medical image data set. The acquisition processor is designed to acquire the medical image data set of the examination object in which the obstacle is situated. The determining processor is designed to determine a property of the obstacle within the examination object by applying the trained artificial neural network to the medical image data set, by assigning a data entry of the data class to the obstacle within the examination object, so the obstacle within the examination object is characterized by the data entry. The third supply processor is designed to supply the property of the obstacle within the examination object as an electronic output. The characterization computer can optionally include a selection processor that selects a method for acquiring a further medical image data set. The characterization computer can optionally include an optimization processor for optimizing the method for acquiring a further medical image data set, according to criterion that can be specified by a user. The second supply processor can optionally include a training unit for training an artificial neural network.

An advantage of the inventive characterization computer essentially corresponds to the advantages of the inventive method for characterizing an obstacle within an examination object, as described above in detail. Features, advantages and alternative embodiments mentioned above are applicable to computers. The functional features of the method are formed by corresponding modules or units of the computer, in particular by hardware modules.

Furthermore, the invention encompasses a medical imaging apparatus having a control computer that includes the aforementioned characterization computer, and a medical data acquisition scanner. The characterization computer is designed to carry out the inventive method for characterizing an obstacle within an examination object. The acquisition scanner is designed to acquire a further medical image data set. The control computer and/or the characterization computer and/or the acquisition scanner typically each have an input, a processor and an output. The characterization computer can be supplied via the input with a database containing at least one data class and/or a trained artificial neural network and/or a medical image data set of the examination object. Further functions, algorithms or parameters required in the method can be supplied to the control computer via the input.

A property of the obstacle and/or a method for acquisition of a further medical image data set and/or further results of an embodiment of the inventive method can be supplied via the output. The control unit and/or the characterization computer and/or the acquisition scanner can be integrated the medical imaging apparatus. The control computer and/or the characterization computer and/or the acquisition scanner can also be installed separately from the medical imaging apparatus. The control computer and/or the characterization computer and/or the acquisition scanner can be connected to the medical imaging apparatus. The control computer and/or the characterization computer and/or the acquisition scanner can be combined into one unit, or can be at least partially independent of each other.

Embodiments of the inventive medical imaging apparatus are analogous to the embodiments of the inventive method. The medical imaging apparatus can have further control components that are necessary and/or advantageous for carrying out the inventive method. The medical imaging apparatus can also be designed to emit control signals and/or to receive and/or to process control signals in order to carry out the inventive method. The characterization computer is preferably part of the control computer of the inventive medical imaging apparatus. Computer programs and further software can be stored on a memory of the control computer and/or the characterization computer. With such programs or software, the processor of the control computer and/or characterization computer and/or acquisition unit automatically controls and carries out the sequence of the inventive method.

The invention also encompasses a non-transitory, computer-readable data storage medium encoded with programming instructions that, when the storage medium is loaded into a computer or computer system of an imaging apparatus, cause the computer or computer system to operate the imaging apparatus in order to implement any or all embodiments of the method according to the invention, as described above.

Examples of electronically readable data carriers are a DVD, a magnetic tape or a USB stick on which electronically readable control information, in particular software, is stored.

The advantages of the inventive medical imaging apparatus and the inventive electronically readable data carrier correspond to the advantages of the inventive method for characterizing an obstacle within an examination object, as described above in detail. Features, advantages or alternative embodiments of the method are applicable to those other aspects of the invention.

BRIEF DESCRIPTION OF THE DRAWINGS

FIG. 1 schematically illustrates an inventive medical imaging apparatus.

FIG. 2 is a flowchart of a first embodiment of the inventive method.

FIG. 3 is a flowchart of a second embodiment of an inventive method.

FIG. 4 is a flowchart of an embodiment for supplying the trained artificial neural network.

DESCRIPTION OF THE PREFERRED EMBODIMENTS

FIG. 1 shows a magnetic resonance apparatus 11 as an example of an inventive medical imaging apparatus 12 for carrying out the inventive method. Basically, the design of the medical imaging apparatus 12 is not restricted to a magnetic resonance apparatus 11, but can also be formed by other medical imaging apparatuses that are known to those skilled in the art, such as computed tomography, PET, SPECT, ultrasound devices, X-ray equipment, C-arm devices, combined medical imaging devices, etc.

The magnetic resonance apparatus 11 has a scanner 13 having a basic field magnet 17 that generates a strong and constant basic magnetic field 18. The scanner 13 has a cylindrical patient-receiving region 14 for receiving a patient 15, with the patient-receiving region 14 being circumferentially surrounded by the scanner 13. The patient 15 can be moved by a patient-positioning device 16 into the patient-receiving region 14. The patient-positioning device 16 has an examination table arranged so as to move inside the scanner 13.

The scanner 13 also has a gradient coil arrangement 19 for spatially encoding the MR signals. The gradient coil arrangement 19 is operated by a gradient controller 28. The scanner 13 also has a radio-frequency (RF) antenna 20, which in the illustrated case is designed as a body coil permanently integrated in the scanner 13. An RF controller 29 operates the RF antenna 20 so as to radiate RF pulses into an examination space, which is essentially formed by the patient-receiving region 14. The radiated RF pulses give certain nuclear spins in the patient 15 a magnetization that causes those excited nuclear spins to be deflected from the alignment produced by the basic magnetic field 18. As these excited nuclear spins relax, and return to alignment with the basic magnetic field 18 they emit RF signals known as MR signals. These MR signals can be detected (received) by the same antenna that radiated the RF pulses, or by a different antenna. These received MR signals are entered into a memory, and can be transformed into image data in a known manner.

For operating the basic field magnet 17, the gradient controller 28 and the RF controller 29, the magnetic resonance apparatus 11 has a control computer 24. The control computer 24 centrally controls the magnetic resonance apparatus 11, such as for carrying out MR control sequences. Furthermore, the control computer 24 has a reconstruction processor (not shown) for reconstructing medical image data from the raw data acquired during the magnetic resonance examination. The magnetic resonance apparatus 11 has a display monitor 25. Control information, such as control parameters and reconstructed image data, can be displayed on the display monitor 25, for example on at least one screen thereof, for a viewer. Furthermore, the magnetic resonance apparatus 11 has an input unit 26 via which a user can enter information and/or control parameters during a scanning process. The control computer 24 can include the gradient controller 28 and/or radio-frequency controller 29 and/or the display monitor 25 and/or input unit 26.

The control computer 24 also has a characterization processor 33 and an acquisition processor 34. The control computer 24 is designed, moreover, for carrying out the method for characterizing an obstacle within an examination object and preferably for acquisition of a further medical image data set. For this purpose the control computer 24 has computer programs and/or software that can be loaded directly into a memory (not shown) of the control computer 24, having program code in order to carry out the method for characterizing an obstacle within an examination object when the computer programs and/or software are/is run in the control computer 24. The control computer 24 has for this purpose a processor (not shown), designed for carrying out the computer programs and/or software. Alternatively, the computer programs and/or software can be stored on an electronically readable data carrier 21 designed separately from the control computer 24 and/or characterization processor 33 and/or acquisition processor 34.

The illustrated magnetic resonance apparatus 11 can of course have further components that magnetic resonance apparatuses conventionally have. The general mode of operation of a magnetic resonance apparatus is known to those skilled in the art, so a detailed description is not necessary herein. The magnetic resonance apparatus 11, together with the control computer 24, is therefore designed for carrying out the inventive method.

The inventive method for characterizing an obstacle within an examination object can also be in the form of the encoded non-transitory data carrier 21.

FIG. 2 is a flowchart of a first embodiment of the inventive method. In method step 110 a database is supplied, comprising at least one data class for a feature for characterizing different obstacles each having at least one data entry for one obstacle respectively. In the following method step 120 a trained artificial neural network is supplied for relationships between the different obstacles, the feature and the medical image data set. In method step 130 the medical image data set is acquired from the examination object comprising the obstacle within the examination object. In method step 140 a property of the obstacle within the examination object is determined by applying the trained artificial neural network to the medical image data set, with a data entry of the data class being assigned to the obstacle within the examination object and the obstacle within the examination object being characterized by the data entry. In method step 150 the property of the obstacle within the examination object is supplied.

The obstacle is characterized by at least one of the following features: material of the obstacle, shape of the obstacle, size of the obstacle, producer of the obstacle, effect of the obstacle on a medical image data set as a function of a medical imaging device and/or recording technique used for generating the medical image data set, a typical position and/or orientation and/or environment of the obstacle within the examination object.

FIG. 3 is a flowchart of a second embodiment of an inventive method. The property of the obstacle within the examination object can be supplied according to method step 150 in such a way that, based thereon, a method for acquisition of a further medical image data set is selected. The selection can optionally comprise method step 165: an optimization of a method for acquisition of a further medical image data set. A criterion specified by a user can be considered for this. In method step 170 a further medical image data set is acquired according to the selected method. The further medical image data set is preferably acquired with the same medical imaging apparatus 12 as the original acquisition of the medical image data set.

If the medical imaging apparatus 12 is designed as a magnetic resonance apparatus 11, the further medical image data set is preferably acquired in method step 170 according to one of following magnetic resonance control sequences and/or recording techniques: TSE, SEMAC, VAT, MAVRIC, STIR, SPAIR, DIXON, saturation pulses with different resonance frequency.

According to this embodiment method step 150, supplying the property of the obstacle, optionally method step 155, can comprise updating the trained artificial neural network while considering the supplied property.

FIG. 4 is a flowchart of an embodiment for supplying the trained artificial neural network. According to this embodiment, method step 120 includes the following steps: in method step 121 a data class is supplied for a feature for characterizing different obstacles, comprising at least one data entry respectively for one obstacle respectively.

In method step 122 a number of medical training image data sets is supplied. In method step 123 the data entries are assigned to the number of medical training image data sets. In method step 124 an artificial neural network is trained using image content of the number of medical training image data sets and the data entries assigned to the plurality of medical training image data sets, with the trained artificial neural network enabling assignment of a data entry to a medical image data set. In method step 125 the trained artificial neural network is supplied for characterizing an obstacle within the examination object.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for characterizing an obstacle within an examination object, comprising:
providing a computer with a database comprising a set of different data classes, each data class from among the set of different data classes being associated with a different respective feature that characterizes a physical property that is common to a plurality of different obstacles, a data class from among the set of data classes comprising at least one respective data entry for each of said different obstacles;
providing said computer with a medical image data set acquired from an examination object comprising an obstacle therein;
providing said computer with a trained artificial neural network that defines and develops relationships between said different obstacles, said feature, and contents of an input medical image data set;
in said computer, applying said trained artificial neural network to said acquired medical image data set by using, as the input medical image data set, the acquired medical image data set to determine a physical property of said obstacle in said examination object, and assigning a data entry from said data class to said obstacle in the examination object so that the physical property of said obstacle identified in accordance with the assigned data entry; and
providing an electronic signal as an output from said computer that represents the obstacle characterized by the assigned data entry.

2. A method as claimed in claim 1, wherein the feature that characterizes the physical property that is common to the plurality of different obstacles is selected from the group consisting of a material of said different obstacles, a shape of said different obstacles, and a size of said different obstacles.

3. A method as claimed in claim 1 comprising in said computer, updating said trained artificial neural network while determining said physical property.

4. A method as claimed in claim 1, comprising, in said computer, selecting a method for acquiring a further medical image data set from the examination object, based on the determined physical property of the obstacle within the examination object.

5. A method as claimed in claim 4, comprising selecting said technique for acquiring said further medical image data set as using said physical property of said obstacle.

6. A method as claimed in claim 4, comprising operating a medical data acquisition scanner in order to acquire said further medical imaging data set according to the selected technique.

7. A method as claimed in claim 6, comprising acquiring said further medical image data set with a same medical imaging scanner as was used to acquire said acquired medical image data set.

8. A method as claimed in claim 6 comprising acquiring said further medical image data set using a magnetic resonance data acquisition scanner, and selecting said method for acquiring said further medical image data set using a magnetic resonance data acquisition technique selected from the group consisting of Turbo Spin Echo (TSE) Slice Encoding Metal Artifact Correction (SEMAC), View Angle Tilting (VAT), Multi Acquisition Variable Resonance Image Combination (MAVRIC), Short T1 Inversion Recovery (STIR), Spectral Attenuated Inversion Recovery (SPAIR), Dixon, and a technique using saturation pulses having different resonance frequencies.

9. A method as claimed in claim 1, comprising providing said trained artificial neural network to said computer by creating said trained artificial neural network in a training computer selected from the group consisting of said computer and another, different computer, by:
   providing said training computer with a training data class comprising data entries for a feature that characterizes a physical property of different obstacles, said training data class comprising at least one training data entry respectively for each of said different obstacles;
   providing said training computer with a plurality of training medical image data sets;
   in said training computer, assigning data entries to the plurality of training medical image data sets;
   training an artificial network in said training computer using an image content of the plurality of training medical image data sets and the training data entries assigned to the plurality of training medical image data sets so as to assign one of said training data entries to a medical image data set provided to the neural network as an input medical image data set, thereby producing said trained artificial neural network; and
   providing the trained artificial neural network from said training computer to said computer.

10. A method as claimed in claim 1, wherein the feature that characterizes the physical property that is common to the plurality of different obstacles is selected from the group consisting of a manufacturer of said different obstacles, and an effect of the respective different obstacles on a medical image data set with regard to at least one of a medical imaging apparatus and data acquisition technique used to generate the medical image data set.

11. A method as claimed in claim 1, wherein applying the trained artificial neural network to further acquired medical image data sets enables an identification of different properties of the different obstacles in accordance with assigned data entries from the set of different data classes.

12. A computer for characterizing an obstacle within an examination object, said computer comprising:
   a processor configured to access a database comprising a set of different data classes, each data class from among the set of different data classes being associated with a different respective feature that characterizes a physical property that is common to a plurality of different obstacles, a data class from among the set of data classes comprising at least one respective data entry for each of said different obstacles;
   an input that receives into said processor a medical image data set acquired from an examination object comprising an obstacle therein;
   a trained artificial neural network that defines and develops relationships between said different obstacles, said feature, and contents of an input medical image data set;
   said processor configured to apply said trained artificial neural network to said acquired medical image data set by using, as the input medical image data set, the acquired medical image data set to determine a physical property of said obstacle in said examination object and assign a data entry from said data class to said physical property of the obstacle in the examination object so that the physical property of said obstacle is identified in accordance with the assigned data entry; and
   an output which said processor provides an electronic signal as an output that represents the obstacle characterized by the assigned data entry.

13. A computer as claimed in claim 12, wherein said processor is configured to select a technique for acquiring a further medical image data set from the examination object based on the determined physical property of the obstacle within the examination object, and to emit a further electronic signal at said output that represents the selected technique.

14. A computer as claimed in claim 13, wherein said processor is configured to operate a medical data acquisition scanner in order to acquire said further medical imaging data set according to the selected technique.

15. A medical imaging apparatus comprising:
   a medical image data acquisition scanner;
   a computer provided with a database comprising a set of different data classes, each data class from among the set of different data classes being associated with a different respective feature that characterizes a physical property that is common to a plurality of different obstacles, a data class from among the set of data classes comprising at least one respective data entry for each of said different obstacles;
   said computer being configured to operate the medical image data acquisition scanner so as to acquire a medical image data set from an examination object comprising an obstacle therein;
   said computer comprising a trained artificial neural network that defines and develops relationships between said different obstacles, said feature, and contents of an input medical image data set;
   said computer being configured to apply said trained artificial neural network to said acquired medical image data set by using, as the input medical image data set, the acquired medical image data set to determine a physical property of said obstacle in said examination object and assign a data entry from said data class to said physical property of the obstacle so that the physical property of said obstacle is identified in accordance with the assigned data entry;
   said computer being configured to provide an electronic signal as an output from said computer that represents the obstacle characterized by the assigned data entry; and
   said computer being configured to select, based on the determined physical property of the obstacle, a technique for acquiring one of the further medical image data sets from said examination object containing said obstacle, and to operate said medical image data acquisition scanner according to the selected technique to acquire said further medical image data set from said examination object containing said obstacle.

16. A medical imaging apparatus as claimed in claim 15 wherein said medical image data acquisition scanner is a magnetic resonance data acquisition scanner.

17. A non-transitory, computer-readable data storage medium encoded with programming instructions, said storage medium being loaded into a computer and said programming instructions causing said computer to:
   access a database comprising a set of different data classes, each data class from among the set of different data classes being associated with a different respective feature that characterizes physical property that is common to a plurality of different obstacles, a data class from among the set of data classes comprising at least one respective data entry for each of said different obstacles;
   receive a medical image data set acquired from an examination object comprising an obstacle therein;

access a trained artificial neural network that defines and develops relationships between said different obstacles, said feature, and contents of an input medical image data set;

apply said trained artificial network to said acquired medical image data set by using, as the input medical image data set, the acquired medical image data set to determine a physical property of said obstacle in said examination object, and assign a data entry from said data class to said obstacle in the examination object so that the physical property of said obstacle is identified in accordance with the assigned data entry; and provide an electronic signal as an output from said computer that represents the obstacle characterized by the assigned data entry.

18. A non-transitory, computer-readable data storage medium as claimed in claim 17 wherein said programming instructions cause said computer to select a method for acquiring a further medical image data set from the examination object, based on the determined property of the obstacle within the examination object.

19. A non-transitory, computer-readable data storage medium as claimed in claim 18 wherein said programming instructions cause said computer to operate a medical data acquisition scanner in order to acquire said further medical imaging data set according to the selected method.

\* \* \* \* \*